(12) United States Patent
Resconi et al.

(10) Patent No.: US 7,858,717 B2
(45) Date of Patent: Dec. 28, 2010

(54) METALLOCENE COMPOUNDS

(75) Inventors: Luigi Resconi, Ferrara (IT); Ilya E. Nifant'ev, Moscow (RU); Pavel V. Ivchenko, Moscow (RU); Vladimir Bagrov, Moscow (RU); Francesca Focante, Filottrano Ancona (IT); Gilberto Moscardi, Ferrara (IT)

(73) Assignee: Basell Polyolefine GmbH, Wesseling (DE)

(*) Notice: Subject to any disclaimer, the term of this patent is extended or adjusted under 35 U.S.C. 154(b) by 0 days.

(21) Appl. No.: 12/225,200

(22) PCT Filed: Mar. 5, 2007

(86) PCT No.: PCT/EP2007/052056
§ 371 (c)(1),
(2), (4) Date: Sep. 16, 2008

(87) PCT Pub. No.: WO2007/107448
PCT Pub. Date: Sep. 27, 2007

(65) Prior Publication Data
US 2009/0171047 A1   Jul. 2, 2009

Related U.S. Application Data

(60) Provisional application No. 60/787,452, filed on Mar. 30, 2006.

(30) Foreign Application Priority Data

Mar. 17, 2006  (EP) ................... 06111299

(51) Int. Cl.
*C08F 4/44* (2006.01)
(52) U.S. Cl. .................... 526/160
(58) Field of Classification Search ........ 526/126, 526/160; 502/153
See application file for complete search history.

(56) References Cited

U.S. PATENT DOCUMENTS

| | | | |
|---|---|---|---|
| 5,698,487 A | 12/1997 | Sacchetti et al. | |
| 5,770,753 A | 6/1998 | Küber et al. | |
| 5,786,432 A | 7/1998 | Küber et al. | |
| 5,840,644 A | 11/1998 | Küber et al. | |
| 5,840,948 A | 11/1998 | Rohrmann et al. | |
| 6,051,727 A | 4/2000 | Küber et al. | |
| 6,057,408 A * | 5/2000 | Winter et al. | 526/160 |
| 6,242,544 B1 | 6/2001 | Küber et al. | |
| 6,255,506 B1 | 7/2001 | Küber et al. | |
| 6,399,533 B2 | 6/2002 | Sacchetti et al. | |
| 6,423,660 B1 | 7/2002 | Albizzati et al. | |
| 6,444,604 B1 | 9/2002 | Albizzati et al. | |
| 6,492,539 B1 | 12/2002 | Bingel et al. | |
| 6,559,252 B1 | 5/2003 | Horton et al. | |
| 6,608,224 B2 | 8/2003 | Resconi et al. | |
| 6,774,194 B2 | 8/2004 | Albizzati et al. | |
| 6,787,618 B1 | 9/2004 | Winter et al. | |
| 6,841,501 B2 | 1/2005 | Resconi et al. | |
| 6,878,786 B2 | 4/2005 | Resconi et al. | |

(Continued)

FOREIGN PATENT DOCUMENTS

| | | |
|---|---|---|
| DE | 19962814 | 6/2001 |
| DE | 19962910 | 7/2001 |
| EP | 576970 | 1/1994 |
| EP | 633272 | 1/1995 |
| EP | 776913 | 6/1997 |
| WO | 91/02012 | 2/1991 |
| WO | 92/00333 | 1/1992 |
| WO | 95/32995 | 12/1995 |
| WO | 98/40331 | 9/1998 |
| WO | 99/21899 | 5/1999 |

(Continued)

OTHER PUBLICATIONS

L. Resconi et al., "Selectivity in Propene Polymerization with Metallocene Catalysts;" *Chem. Rev.*, vol. 100(4), p. 1253-1345 (2000).

(Continued)

*Primary Examiner*—Ling-Siu Choi
*Assistant Examiner*—Sonya Wright
(74) *Attorney, Agent, or Firm*—William R. Reid

(57) ABSTRACT

A bridged metallocene compound of formula (I)

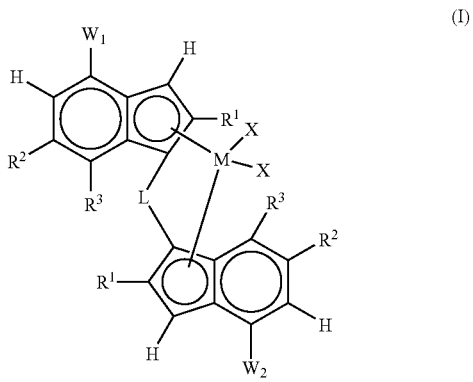

wherein:
M is an atom of a transition metal selected from those belonging to group 3, 4, or to the lanthanide or actinide groups in the Periodic Table of the Elements;
X, equal to or different from each other, is a hydrogen atom, a halogen atom, a R, OR, $OSO_2CF_3$, OCOR, SR, $NR_2$ or $PR_2$ group; L is a divalent bridging group;
$R^1$ and $R^2$, equal to each other, are $C_1$-$C_{40}$ hydrocarbon radical; R3 is hydrogen or a are $C_1$-$C_{40}$ hydrocarbon radical and W is an aromatic 5 or 6 membered ring.

16 Claims, No Drawings

U.S. PATENT DOCUMENTS

| | | |
|---|---|---|
| 6,953,829 B2 | 10/2005 | Kratzer et al. |
| 6,963,017 B2 | 11/2005 | Bingel et al. |
| 7,038,070 B2 | 5/2006 | Bingel et al. |
| 7,053,160 B1 | 5/2006 | Bingel et al. |
| 7,101,940 B2 | 9/2006 | Schottek et al. |
| 7,141,527 B1 | 11/2006 | Van Baar et al. |
| 7,452,949 B2 | 11/2008 | Okumura et al. |
| 2006/0052553 A1 | 3/2006 | Resconi et al. |
| 2006/0252637 A1 | 11/2006 | Okumura |

FOREIGN PATENT DOCUMENTS

| | | |
|---|---|---|
| WO | 00/31090 | 6/2000 |
| WO | 01/21674 | 3/2001 |
| WO | 01/62764 | 8/2001 |
| WO | 03/050131 | 6/2003 |
| WO | 2004/050724 | 6/2004 |
| WO | 2004/106351 | 12/2004 |
| WO | 2005/058916 | 6/2005 |
| WO | 2006/097500 | 9/2006 |
| WO | 2007/116034 | 10/2007 |

OTHER PUBLICATIONS

C. Carman et al., "Monomer Sequence Distribution in Ethylene-Propylene Rubber Measured by $^{13}$C NMR. 3. Use of Reaction Probability Model," *Macromolecules*, vol. 10(3), p. 536-544 (1977).

M. Kakugo et al., "$^{13}$C NMR Determination of Monomer Sequence Distribution in Ethylene-Propylene Copolymers Prepared with $\delta$-TiCl$_3$-Al(C$_2$H$_5$)$_2$Cl," *Macromolecules*, vol. 15(4), p. 1150-1152 (1982).

I. Triotto et al., "$^{13}$C NMR Studies of Ethylene-Propylene Copolymers Prepared with Homogeneous Metallocene-Based Ziegler-Natta Catalysts," *Macromolecules*, vol. 28(9), p. 3342-3350 (1995).

F. Forlini et al., "$^{13}$C NMR studies of zirconocene-catalyzed propylene/1-hexene copolymers: in-depth investigation of the effect of solvent polarity," *Macromol. Chem. Phys.*, vol. 201(4), p. 401-408 (2000).

V. Izmer et al., "Palladium-Catalyzed Pathways to Aryl-Substituted Indenes: Efficient Synthesis of Ligands and the Respective *ansa*-Zirconocenes," *Organometallics*, vol. 25(5), p. 1217-1229 (2006).

J. Randall, "A Review of High Resolution Liquid $^{13}$Carbon Nuclear Magnetic Resonance Characterizations of Ethylene-Based Polymers," *JMS-Rev. Macromol. Chem. Phys.*, vol. C29(2&3), p. 201-317 (1989).

J. Randall, "A $^{13}$C NMR Determination of the Comonomer Sequence Distributions in Propylene-Butene-1 Copolymers," *Macromolecules*, vol. 11(3), p. 592-597 (1978).

\* cited by examiner

METALLOCENE COMPOUNDS

This application is the U.S. national phase of International Application PCT/EP2007/052056, filed Mar. 5, 2007, claiming priority to European Application 06111299.1 filed Mar. 17, 2006 and the benefit under 35 U.S.C. 119(e) of U.S. Provisional Application No. 60/787,452, filed Mar. 30, 2006; the disclosures of International Application PCT/EP2007/052056, European Application 06111299.1 and U.S. Provisional Application No. 60/787,452, each as filed, are incorporated herein by reference.

The present invention relates to a new class of metallocene compounds having a particular substitution pattern able to polymerize alpha olefins in high yields to give a polymer having an high molecular weight. The present invention further relates to the catalyst system thereof and the polymerization process therefrom.

Metallocene compounds are well known in the art as catalyst components for the polymerization of olefins. WO04/106351 relates to a class of bis indenyl metallocene compounds substituted in positions 2, 4 and 6. The compounds disclosed have $C_1$ symmetry i.e. the two indenyl are substituted in a different way, in particular the substituents in position 2 of the indenyl ring are different. This implies that the synthesis of these compounds is quite complicated for the reason that two different indenyl moieties have to be prepared. U.S. Pat. No. 5,840,948 relates to some bis indenyl based metallocene compounds containing 2-metyl, 4,6 diisopropyl moiety and 2,4,6 trimethylindenyl moiety. However the particular substitution patter of the compounds of the present invention is not suggested.

Thus there still is the need to find a new class of metallocene compounds able to polymerize olefins in higher yields and to produce polymers having very high molecular weight especially when the process is carried out at high temperature.

An object of the present invention is a bridged metallocene compound of formula (I)

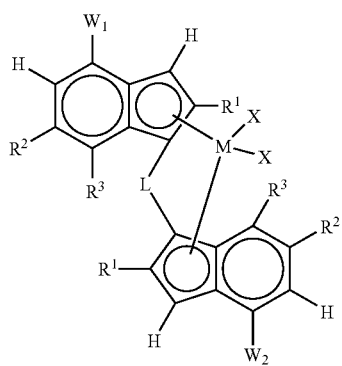

wherein:

M is an atom of a transition metal selected from those belonging to group 3, 4, or to the lanthanide or actinide groups in the Periodic Table of the Elements; preferably M is zirconium, titanium or hafnium;

X, equal to or different from each other, is a hydrogen atom, a halogen atom, a R, OR, $OSO_2CF_3$, OCOR, SR, $NR_2$ or $PR_2$ group wherein R is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical; optionally containing heteroatoms belonging to groups 13-17 of the Periodic Table of the Elements; or two X groups can be joined together to form a group OR'O wherein R' is a $C_1$-$C_{20}$-alkylidene, $C_6$-$C_{20}$-arylidene, $C_7$-$C_{20}$-alkylarylidene, or $C_7$-$C_{20}$-arylalkylidene radical; preferably X is a hydrogen atom, a halogen atom or R group; more preferably X is chlorine or a methyl radical;

L is a divalent bridging group selected from $C_1$-$C_{20}$ alkylidene, $C_3$-$C_{20}$ cycloalkylidene, $C_6$-$C_{20}$ arylidene, $C_7$-$C_{20}$ alkylarylidene, or a $C_7$-$C_{20}$ arylalkylidene radicals, optionally containing heteroatoms belonging to groups 13-17 of the Periodic Table of the Elements, or it is a silylidene radical containing up to 5 silicon atoms; preferably L is $Si(R^{11})_2$ wherein $R^{11}$ is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical; more preferably L is $Si(CH_3)_2$ or $SiPh_2$;

$R^1$, equal to each other, are $C_1$-$C_{40}$ hydrocarbon radical optionally containing heteroatoms belonging to groups 13-17 of the Periodic Table of the Elements such as methyl or ethyl radical; preferably $R^1$ is a linear $C_1$-$C_{20}$-alkyl, such as a methyl, or ethyl radical;

$R^2$, equal to or different from each other, are $C_3$-$C_{40}$ branched, cyclic or acyclic, alkyl, alkenyl, or alkynyl radicals optionally containing heteroatoms belonging to groups 13-17 of the periodic table of the elements; preferably $R^2$, equal to or different from each other, are $C(R^{19})_2R^{18}$ group;

wherein $R^{18}$ equal to or different from each other, are hydrogen atoms or a $C_1$-$C_{40}$ hydrocarbon radical optionally containing one or more heteroatoms belonging to groups 13-17 of the Periodic Table of the Elements; preferably $R^{18}$ is a hydrogen atom or a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical, optionally containing one or more heteroatoms belonging to groups 13-17 of the Periodic Table of the Elements; more preferably $R^{18}$ is a linear or branched, $C_1$-$C_{20}$-alkyl radical; more preferably $R^{18}$ is a methyl or ethyl radical;

$R^{19}$ is a $C_1$-$C_{40}$ hydrocarbon radical optionally containing one or more heteroatoms belonging to groups 13-17 of the Periodic Table of the Elements; preferably $R^{19}$ is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical, optionally containing one or more heteroatoms belonging to groups 13-17 of the Periodic Table of the Elements; or two $R^{19}$ radical can join together to form a $C_4$-$C_6$ membered ring wherein optionally one carbon atom can be substituted with a nitrogen, sulfur or oxygen atom; more preferably $R^{19}$ is a linear or branched, $C_1$-$C_{20}$-alkyl radical; more preferably $R^{19}$ is a methyl or ethyl radical; examples of group $C(R^{19})_2R^{18}$ are tert-butyl, isopropyl, cyclopentyl, cyclohexyl, 2 furanyl radicals; linear or branched $C_1$-$C_{40}$-alkyl radicals, such as methyl, ethyl, isopropyl, trimethylsilyl, or tertbutyl radical; preferably the two $R^2$ groups are the same;

$R^3$, equal to or different from each other, are hydrogen atoms or $C_1$-$C_{40}$ hydrocarbon radicals belonging to groups 13-17 of the periodic table of the elements; preferably $R^3$ is a hydrogen atom or a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals belonging to groups 13-17 of the periodic table of the elements; more preferably $R^3$, equal to or different from each other, are hydrogen atoms or linear or branched $C_1$-$C_{40}$-alkyl radicals, even more preferably $R^3$ are hydrogen atoms.

$W^1$ and $W^2$, equal or different from each other, are aromatic 5 or 6 membered rings that can contain heteroatoms belonging to groups 15-16 of the Periodic Table of the Elements; the valence of each atom of said ring is substituted with hydrogen atom or it can optionally be substituted with $R^5$ groups, wherein $R^5$, equal to or different from each other, are $C_1$-$C_{40}$ hydrocarbon radicals optionally containing heteroatoms belonging to groups 13-17 of the Periodic Table of the Elements; preferably $R^5$, are linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals optionally containing heteroatoms belonging to groups 13-17 of the Periodic Table of the Elements;

Preferably $W^1$ and $W^2$ are selected from the group comprising the following moieties of formula (Wa), (Wb) and (Wc):

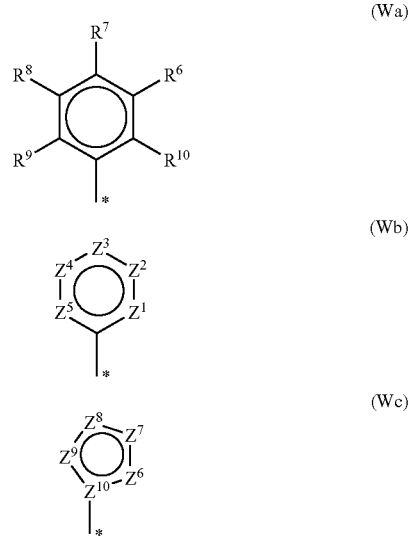

wherein the * represents the point in which the moiety is bonded to the indenyl moiety of the compound of formula (I);

$R^6$, $R^7$, $R^8$, $R^9$ and $R^{10}$, equal to or different from each other, are hydrogen atoms or $C_1$-$C_{40}$ hydrocarbon radicals optionally containing heteroatoms belonging to groups 13-17 of the Periodic Table of the Elements; preferably $R^6$, $R^7$, $R^8$, $R^9$ and $R^{10}$, are hydrogen atoms or linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals optionally containing heteroatoms belonging to groups 13-17 of the Periodic Table of the Elements;

$Z^1$ is a nitrogen atom or a $CR^{10}$ group; $Z^2$ is a nitrogen atom or a $CR^6$ group; $Z^3$ is a nitrogen atom or a $CR^7$ group; $Z^4$ is a nitrogen atom or a $CR^8$ group; $Z^5$ is a nitrogen atom or a $CR^9$ group; provided that no more than 2 groups among $Z^1$, $Z^2$, $Z^3$, $Z^4$ and $Z^5$ are nitrogen atoms, preferably no more than one group among $Z^1$, $Z^2$, $Z^{3, Z4}$ and $Z^5$ is a nitrogen atom;

$Z^6$ is an oxygen atom, a sulfur atom, a $NR^{13}$ group or a $CR^{13}$ group; $Z^7$ is an oxygen atom, a sulfur atom, a $NR^{14}$ group or a $CR^{14}$ group; $Z^8$ is an oxygen atom, a sulfur atom, a $NR^{15}$ group or a $CR^{15}$ group; $Z^9$ is an oxygen atom, a sulfur atom, a $NR^{16}$ group or a $CR^{16}$ group;

$Z^{10}$ is a nitrogen atom or a carbon atom that bonds the indenyl moiety of the structure of formula (I); with the proviso that not more than 1 group among $Z^6$, $Z^7$, $Z^8$, $Z^9$ or $Z^{10}$ is a sulfur atom, an oxygen atom or a nitrogen-containing group atom selected from $NR^{13}$, $NR^{14}$, $NR^{15}$, $NR^{16}$, and a nitrogen atom; $R^{13}$, $R^{14}$, $R^{15}$ and $R^{16}$, equal to or different from each other, are hydrogen atoms or $C_1$-$C_{40}$ hydrocarbon radicals optionally containing heteroatoms belonging to groups 13-17 of the Periodic Table of the Elements; preferably $R^{13}$, $R^{14}$, $R^{15}$ and $R^{16}$, are hydrogen atoms or linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radicals optionally containing heteroatoms belonging to groups 13-17 of the Periodic Table of the Elements; more preferably $R^{13}$, $R^{14}$, $R^{15}$ and $R^{16}$-are hydrogen atoms, $C_1$-$C_{40}$-alkyl or $C_6$-$C_{40}$-aryl radicals;

In the moiety of formula (Wa), in a preferred embodiment, $R^7$ is a $C_1$-$C_{40}$-alkyl radical, preferably a branched $C_1$-$C_{40}$-alkyl radical, more preferably $R^7$ is a branched $C_1$-$C_{40}$-alkyl radical wherein the carbon atom in position alpha is a tertiary carbon atom such as a tertbutyl radical, and $R^6$, $R^8$, $R^9$ and $R^{10}$ are hydrogen atoms;

In a further preferred embodiment $R^{10}$ and $R^8$ are $C_1$-$C_{40}$-alkyl radicals, preferably they are linear $C_1$-$C_{40}$ alkyl radicals such as methyl radicals and $R^7$, $R^8$ and $R^9$ are hydrogen radicals: In a further preferred embodiment $R^6$, $R^7$ and $R^8$ are linear or branched $C_1$-$C_{40}$-alkyl radicals such as methyl or tertbutyl radicals and $R^{10}$ and $R^9$ are hydrogen atoms.

In a further preferred embodiment $R^6$, $R^7$, $R^8$, $R^9$ and $R^{10}$ are hydrogen atoms;

In the moiety of formula (Wb), in a preferred embodiment, $Z^1$ is a nitrogen atom and $Z^2$, $Z^3$, $Z^4$ and $Z^5$ are respectively $CR^6$, $CR^7$, $CR^8$ and $CR^9$ wherein the meaning of $R^6$, $R^7$, $R^8$, and $R^9$ is described above; in a further preferred embodiment $Z^3$ is a nitrogen atom and $Z^1$, $Z^2$, $Z^4$ and $Z^5$ are respectively $CR^{10}$, $CR^6$, $CR^8$ and $CR^9$ wherein the meaning of $R^{10}$, $R^6$, $R^8$, and $R^9$ is described above; in a further preferred embodiment $Z^2$ is a nitrogen atom and $Z^1$, $Z^3$, $Z^4$ and $Z^5$ are respectively $CR^{10}$, $CR^7$, $CR^8$ and $CR^9$ wherein the meaning of $R^{10}$, $R^7$, $R^8$, and $R^9$ is described above;

In the moiety of formula (Wc) in a preferred embodiment $Z^6$ is an oxygen atom, a sulfur atom, a $NR^{16}$ group; preferably it is a sulfur atom or a $NR^{16}$; wherein $R^{16}$ is preferably a $C_1$-$C_{40}$-alkyl radical; more preferably $Z^6$ is a sulfur atom; and $Z^7$, $Z^8$, $Z^9$ and $Z^{10}$ are respectively a $CR^{14}$, $CR^{15}$, $CR^{16}$ and a carbon atom, wherein $R^{14}$ is a hydrogen atom or a $C_1$-$C_{40}$-alkyl radical such as methyl or ethyl; and $R^{15}$ and $R^{16}$ are hydrogen atoms or $C_1$-$C_{40}$-alkyl radicals.

In a preferred embodiment of the present invention in the compounds of formula (I) $T^1$ and $T^4$, equal to or different from each other, are an $OR^2$, or a $SR^2$ wherein $R^2$ is described above and $T^2$ and $T^3$, equal to or different from each other, are linear $C_1$-$C_{40}$-alkyl alkyl radicals, such as methyl or ethyl radicals.

In a further preferred embodiment $T^1$ and $T^4$, equal to or different from each other, are an $OR^2$, a $SR^2$ or a $C(R^{18})_3$ group; preferably $T^1$ and $T^4$ are an $OR^2$ or an $SR^2$ groups; and $T^2$ and $T^3$ equal to or different from each other are a $C(R^{19})_2$ $R^{18}$ group wherein $R^{18}$ has been described above and $R^{19}$ is a $C_1$-$C_{40}$ hydrocarbon radical optionally containing one or more heteroatoms belonging to groups 13-17 of the Periodic Table of the Elements; preferably $R^{19}$ is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical, optionally containing one or more heteroatoms belonging to groups 13-17 of the Periodic Table of the Elements; or two $R^{19}$ radical can join together to form a $C_4$-$C_6$ membered ring wherein optionally one carbon atom can be substituted with a nitrogen, sulfur or oxygen atom; more preferably $R^{19}$ is a linear or branched, $C_1$-$C_{20}$-alkyl radical; more preferably $R^{19}$ is a methyl or ethyl radical; examples of group $C(R^{19})_2R^{18}$ are tert-butyl, isopropyl, cyclopentyl, cyclohexyl, 2 furanyl radicals;

A preferred class of the compounds of formula (I) is represented by formula (IIa):

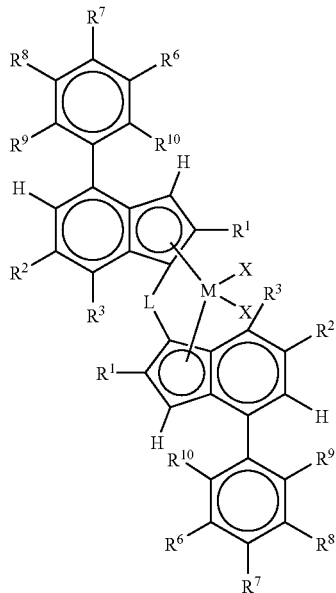

(IIa)

Wherein M, L, X, $R^1$, $R^2$, $R^3$, $R^6$, $R^7$, $R^8$, $R^9$ and $R^{10}$ have the meaning reported above.

A further preferred class of compounds of formula (I) has formula (IIb)

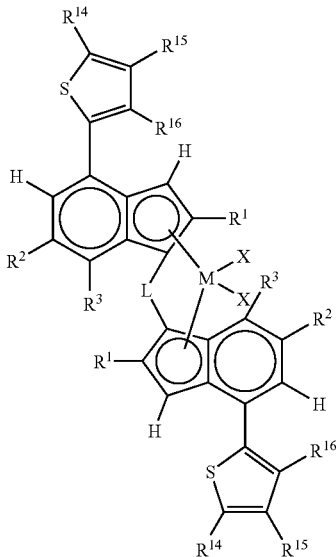

(IIb)

Wherein M, L, X, $R^1$, $R^2$, $R^3$, $R^{14}$, $R^{15}$, $R^{16}$ have the meaning reported above.

Examples of compounds having formula (I) are as follows racemic-Me$_2$Si(2-methyl-4-phenyl-6-tert-butylinden-1-yl)$_2$ZrCl$_2$ racemic-Me$_2$Si(2-methyl-4-(tert-butylphenyl)-6-tert-butylinden-1-yl)$_2$ZrCl$_2$ racemic-Me$_2$Si(2-methyl-4-(thiophen-2-yl)-6-tert-butylinden-1-yl)$_2$ZrCl$_2$ racemic-Me$_2$Si(2-methyl-4-(5-methylthiophen-2-yl)-6-tert-butylinden-1-yl)$_2$ZrCl$_2$ racemic-Me$_2$Si(2-methyl-4-(benzothiophen-2-yl)-6-tert-butylinden-1-yl)$_2$ZrCl$_2$ racemic-Me$_2$Si(2-methyl-4-(4-pyridyl)-6-tert-butylinden-1-yl)$_2$ZrCl$_2$ racemic-Me$_2$Si(2-methyl-4-(2,5-dimethylphenyl)-6-tert-butylinden-1-yl)$_2$ZrCl$_2$ racemic-Me$_2$Si(2-ethyl-4-phenyl-6-tert-butylinden-1-yl)$_2$ZrCl$_2$ racemic-Me$_2$Si(2-n-propyl-4-phenyl-6-tert-butylinden-1-yl)$_2$ZrCl2 racemic-anti-Me$_2$Si(2-methyl-4-phenyl-6-tert-butylinden-1-yl)(2-methyl-4-(5-methylthiophen-2-yl)-6-tert-butyl-inden-1-yl)ZrCl$_2$ and their correspondent dimethyl derivatives and further the corresponding titanium, and hafnium compounds.

Preferably the metallocene compounds object of the present invention are in their racemic(rac) or anti-racemic form.

For the purpose of the present invention the term "racemic (rac) form" means that the same substituents on the two cyclopentadienyl moieties are on the opposite side with respect to the plane containing the zirconium and the centre of the said cyclopentadienyl moieties. "anti-racemic form" means that the bulkier substituents of the two cyclopentadienyl moieties on the metallocene compound are on the opposite side with respect to the plane containing the zirconium and the centre of the said cyclopentadienyl moieties as shown in the following compound:

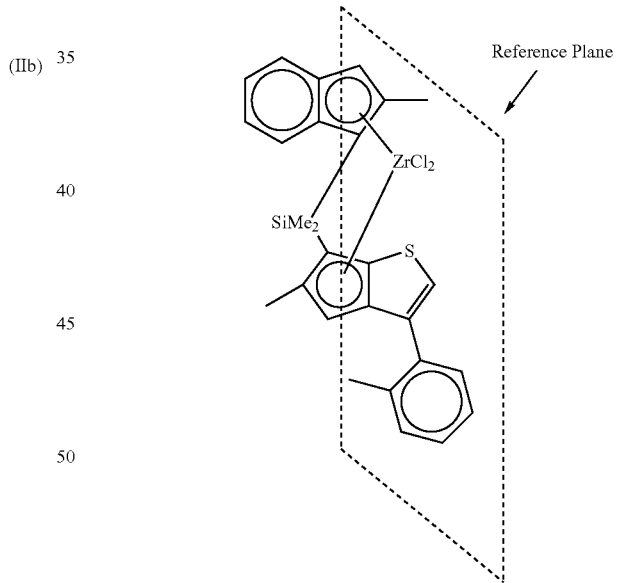

A further object of the present invention is a catalyst system for the polymerization of olefins obtainable by contacting:

a) a metallocene compound of formula (I);
b) at least an alumoxane or a compound able to form an alkylmetallocene cation; and
c) optionally an organo aluminum compound.

Preferably the metallocene compounds have formulas selected from (Ia), (IIa) or (IIb).

Alumoxanes used as component b) in the catalyst system according to the present invention can be obtained by reacting water with an organo-aluminium compound of formula H$_j$AlU$_{3-j}$ or H$_j$Al$_2$U$_{6-j}$, where the U substituents, same or different, are hydrogen atoms, halogen atoms, C$_1$-C$_{20}$-alkyl, C$_3$-C$_{20}$-cycloalkyl, C$_6$-C$_{20}$-aryl, C$_7$-C$_{20}$-alkylaryl or C$_7$-C$_{20}$-arylalkyl radicals, optionally containing silicon or germanium atoms, with the proviso that at least one U is different from halogen, and j ranges from 0 to 1, being also a non-integer number. In this reaction the molar ratio of Al/water is preferably comprised between 1:1 and 100:1.

The alumoxanes used in the catalyst system according to the invention are considered to be linear, branched or cyclic compounds containing at least one group of the type:

wherein the substituents U, same or different, are defined above.

In particular, alumoxanes of the formula:

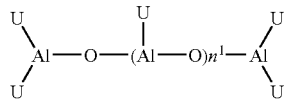

can be used in the case of linear compounds, wherein n$^1$ is 0 or an integer of from 1 to 40 and the substituents U are defined as above; or alumoxanes of the formula:

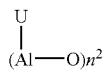

can be used in the case of cyclic compounds, wherein n$^2$ is an integer from 2 to 40 and the U substituents are defined as above.

Examples of alumoxanes suitable for use according to the present invention are methylalumoxane (MAO), tetra-(isobutyl)alumoxane (TIBAO), tetra-(2,4,4-trimethyl-pentyl)alumoxane (TIOAO), tetra-(2,3-dimethylbutyl)alumoxane (TDMBAO) and tetra-(2,3,3-trimethylbutyl)alumoxane (TTMBAO).

Particularly interesting cocatalysts are those described in WO 99/21899 and in WO01/21674 in which the alkyl and aryl groups have specific branched patterns.

Non-limiting examples of aluminium compounds that can be reacted with water to give suitable alumoxanes (b), described in WO 99/21899 and WO01/21674, are:

tris(2,3,3-trimethyl-butyl)aluminium, tris(2,3-dimethyl-hexyl)aluminium, tris(2,3-dimethyl-butyl)aluminium, tris(2,3-dimethyl-pentyl)aluminium, tris(2,3-dimethyl-heptyl)aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl)aluminium, tris(2-ethyl-3-methyl-butyl)aluminium, tris(2-ethyl-3-methyl-pentyl)aluminium, tris(2,3-diethyl-pentyl)aluminium, tris(2-propyl-3-methyl-butyl)aluminium, tris(2-isopropyl-3-methyl-butyl)aluminium, tris(2-isobutyl-3-methyl-pentyl)aluminium, tris(2,3,3-trimethyl-pentyl)aluminium, tris(2,3,3-trimethyl-hexyl)aluminium, tris(2-ethyl-3,3-dimethyl-butyl)aluminium, tris(2-ethyl-3,3-dimethyl-pentyl)aluminium, tris(2-isopropyl-3,3-dimethyl-butyl)aluminium, tris(2-trimethylsilyl-propyl)aluminium, tris(2-methyl-3-phenyl-butyl)aluminium, tris(2-ethyl-3-phenyl-butyl)aluminium, tris(2,3-dimethyl-3-phenyl-butyl)aluminium, tris(2-phenyl-propyl)aluminium, tris[2-(4-fluoro-phenyl)-propyl]aluminium, tris[2-(4-chloro-phenyl)-propyl]aluminium, tris[2-(3-isopropyl-phenyl)-propyl]aluminium, tris(2-phenyl-butyl)aluminium, tris(3-methyl-2-phenyl-butyl)aluminium, tris(2-phenyl-pentyl)aluminium, tris[2-(pentafluorophenyl)-propyl]aluminium, tris[2,2-diphenyl-ethyl]aluminium and tris[2-phenyl-2-methyl-propyl]aluminium, as well as the corresponding compounds wherein one of the hydrocarbyl groups is replaced with a hydrogen atom, and those wherein one or two of the hydrocarbyl groups are replaced with an isobutyl group.

Amongst the above aluminium compounds, trimethylaluminium (TMA), triisobutylaluminium (TIBA), tris(2,4,4-trimethyl-pentyl)aluminium (TIOA), tris(2,3-dimethylbutyl)aluminium (TDMBA) and tris(2,3,3-trimethylbutyl)aluminium (TTMBA) are preferred.

Non-limiting examples of compounds able to form an alkylmetallocene cation are compounds of formula D$^+$E$^-$, wherein D$^+$ is a Brønsted acid, able to donate a proton and to react irreversibly with a substituent X of the metallocene of formula (I) and E$^-$ is a compatible anion, which is able to stabilize the active catalytic species originating from the reaction of the two compounds, and which is sufficiently labile to be removed by an olefinic monomer. Preferably, the anion E$^-$ comprises one or more boron atoms. More preferably, the anion E$^-$ is an anion of the formula BAr$_4^{(-)}$, wherein the substituents Ar which can be identical or different are aryl radicals such as phenyl, pentafluorophenyl or bis(trifluoromethyl)phenyl. Tetrakis-pentafluorophenyl borate is particularly preferred compound, as described in WO 91/02012. Moreover, compounds of formula BAr$_3$ can be conveniently used.

Compounds of this type are described, for example, in the International patent application WO 92/00333. Other examples of compounds able to form an alkylmetallocene cation are compounds of formula BAr$_3$P wherein P is a substituted or unsubstituted pyrrol radical. These compounds are described in WO01/62764. Compounds containing boron atoms can be conveniently supported according to the description of DE-A-19962814 and DE-A-19962815. All these compounds containing boron atoms can be used in a molar ratio between boron and the metal of the metallocene comprised between about 1:1 and about 10:1; preferably 1:1 and 2.1; more preferably about 1:1.

Non limiting examples of compounds of formula D$^+$E$^-$ are:
Tributylammonium tetrakis(pentafluorophenyl)borate,
Tributylammonium tetrakis(pentafluorophenyl)aluminate,
Tributylammonium tetrakis(trifluoromethylphenyl)borate,
Tributylammonium tetrakis(4-fluorophenyl)borate,
Dimethylbenzylammonium-tetrakis(pentafluorophenyl)borate,
Dimethylhexylammonium-tetrakis(pentafluorophenyl)borate,
N,N-Dimethylanilinium tetrakis(pentafluorophenyl)borate,
N,N-Dimethylanilinium tetrakis(pentafluorophenyl)aluminate,
Dimethylbenzylammonium-tetrakis(pentafluorophenyl)borate,
Dimethylhexylammonium-tetrakis(pentafluorophenyl)borate,
Di(propyl)ammoniumte tetrakis(pentafluorophenyl)borate,
Di(cyclohexyl)ammonium tetrakis(pentafluorophenyl)borate,
Triphenylcarbenium tetrakis(pentafluorophenyl)borate, Triphenylcarbenium tetrakis(pentafluorophenyl)aluminate,
Ferrocenium tetrakis(pentafluorophenyl)borate,
Ferrocenium tetrakis(pentafluorophenyl)aluminate.

Organic aluminum compounds used as compound c) are those of formula $H_jAlU_{3-j}$ or $H_jAl_2U_{6-j}$ as described above.

The catalysts of the present invention can also be supported on an inert carrier. This is achieved by depositing the metallocene compound a) or the product of the reaction thereof with the component b), or the component b) and then the metallocene compound a) on an inert support. The support can be a porous solid such as talc, a sheet silicate, an inorganic oxide or a finely divided polymer powder (e.g. polyolefin). Suitable inorganic oxides may be found among the oxides of elements of groups 2, 3, 4, 5, 13, 14, 15 and 16 of the Periodic Table of the Elements. Examples of oxides preferred as supports include silicon dioxide, aluminum oxide, and also mixed oxides of the elements calcium, aluminum, silicon, magnesium or titanium and also corresponding oxide mixtures, magnesium halides, styrene/divinylbenzene copolymers, polyethylene or polypropylene. Other inorganic oxides which can be used alone or in combination with the above-mentioned preferred oxidic supports are, for example, MgO, $ZrO_2$, $TiO_2$ or $B_2O_3$.

A suitable class of supports which can be used is that constituted by porous organic supports functionalized with groups having active hydrogen atoms. Particularly suitable are those in which the organic support is a partially crosslinked styrene polymer. Supports of this type are described in European application EP-633 272.

Another class of inert supports particularly suitable for use according to the invention is that of polyolefin porous prepolymers, particularly polyethylene.

A further suitable class of inert supports for use according to the invention is that of porous magnesium halides such as those described in International application WO 95/32995.

The support materials used preferably have a specific surface area in the range from 10 to 1000 $m^2/g$, a pore volume in the range from 0.1 to 5 ml/g and a mean particle size of from 1 to 500 μm. Preference is given to supports having a specific surface area in the range from 50 to 500 $m^2/g$, a pore volume in the range from 0.5 to 3.5 ml/g and a mean particle size in the range from 5 to 350 μm. Particular preference is given to supports having a specific surface area in the range from 200 to 400 $m^2/g$, a pore volume in the range from 0.8 to 3.0 ml/g and a mean particle size of from 10 to 300 μm.

The inorganic support can be subjected to a thermal treatment, e.g. to remove adsorbed water. Such a drying treatment is generally carried out at from 80 to 300° C., preferably from 100 to 200° C., with drying at from 100 to 200° C. preferably being carried out under reduced pressure and/or a blanket of inert gas (e.g. nitrogen), or the inorganic support can be calcined at from 200 to 1 000° C. to produce the desired structure of the solid and/or set the desired OH concentration on the surface. The support can also be treated chemically using customary desiccants such as metal alkyls, preferably aluminum alkyls, chlorosilanes or $SiCl_4$, or else methylaluminoxane. Appropriate treatment methods are described, for example, in WO 00/31090.

The inorganic support material can also be chemically modified. For example, treatment of silica gel with $(NH_4)_2SiF_6$ leads to fluorination of the silica gel surface, or treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and are preferably likewise freed of adhering moisture, solvent residues or other impurities by means of appropriate purification and drying operations before use. It is also possible to use functionalized polymer supports, e.g. supports based on polystyrene, via whose functional groups, for example ammonium or hydroxy groups, at least one of the catalyst components can be immobilized. The solid compound obtained by supporting the catalyst system object of the present invention on a carrier in combination with the further addition of the alkylaluminium compound either as such or prereacted with water if necessary, can be usefully employed in the gas-phase or slurry polymerization.

The catalyst system of the present invention can be used also in a solution polymerization process.

For the purpose of the present invention the term solution polymerization means preferably that the polymer is fully soluble in the polymerization medium at the polymerization temperature used, and in a concentration range of at least 5% by weight; more preferably from 5 to 50% by weight.

In order to have the polymer completely soluble in the polymerization medium, a mixtures of monomers for copolymers or only one monomer for homopolymers in the presence of an inert solvent can be used. This solvent can be an aliphatic or cycloaliphatic hydrocarbon such as hexane, heptane isooctane, cyclohexane and methylcyclohexane. It is also possible to use mineral spirit or a hydrogenated diesel oil fraction. Also aromatic hydrocarbons can be used such as toluene. Preferred solvents to be used are cyclohexane and methylcyclohexane. In case propylene is used as monomer for the obtainment of propylene copolymers in solution polymerization process, the propylene content in the liquid phase of the polymerization medium preferably ranges from 5% to 60% by weight; more preferably from 20% to 50% by weight.

The catalyst system comprising the metallocene compound of formula (I) can be used for polymerizing olefins, in particular alpha-olefins in high yields to give polymers having high molecular weight. Therefore a further object of the present invention is a process for preparing a alpha-olefin polymer comprising contacting under polymerization conditions one or more alpha-olefins of formula $CH_2=CHA$ wherein A is hydrogen or a $C_1$-$C_{20}$ alkyl radical, in the presence of a catalyst system as described above.

Non limitative examples of alpha-olefins of formula $CH_2=CHA$ are: ethylene, propylene, 1-butene, 1-hexene, 1-octene and 4-methyl-1-pentene, preferred alpha olefins are ethylene, propylene and 1-butene.

The metallocene compounds of formula (I) object of the present invention are particularly suitable for the homo and copolymerization of propylene. In fact, the metallocene-based catalyst system of the present invention when used for homo or copolymerizing propylene are able to give polymers having a high molecular weight in high yields also at high temperatures rendering thus possible to use it in the industrial plants that use polymerization temperatures higher than 50° C. and that can be comprised between 600 and 200° C., preferably between 80° C. and 120° C.

As said above, the metallocene compounds of formula (I) are particularly suitable for the copolymerization of propylene, therefore a further object of the present invention is a process for the preparation of propylene copolymers comprising the step of contacting, under polymerization conditions, propylene with ethylene or one or more alpha olefins of formula $CH_2=CHA^1$, wherein $A^1$ is a $C_2$-$C_{20}$ alkyl radical, in the presence of a catalyst system described above. This process is preferably carried out in solution as described above.

Examples of alpha olefins of formula $CH_2=CHA^1$ are ethylene, 1-butene, 1-hexene, 1-octene and 4-methyl-1-pentene, preferred alpha olefins are ethylene and 1-butene; more preferred alpha olefin is ethylene.

The content of alpha-olefins derived units in the propylene copolymer object of the present invention ranges from 0.1 to 90% by mol; preferably it ranges from 5% by mol to 70% by mol; more preferably it ranges from 10% by mol to 60% by mol.

The metallocene compounds of the present invention are also particularly suitable for the preparation of copolymers of ethylene and higher alpha olefins, such as propylene, 1-butene, 1-hexene, 1-octene. The copolymers have a comonomer content ranging from 5 to 50% by mol. Particularly preferred are ethylene/1-butene copolymer having a content of 1-butene derive units ranging from 5 to 50% by mol.

As explained above the process for the polymerization of olefins according to the invention can be carried out in the liquid phase in the presence or absence of an inert hydrocarbon solvent, such as in in slurry, or in the gas phase. The hydrocarbon solvent can either be aromatic such as toluene, or aliphatic such as propane, hexane, heptane, isobutane or cyclohexane.

As a general rule, the polymerization temperature is generally comprised between −100° C. and +200° C. preferably comprised between 60° and 200° C., more preferably between 80° C. and 120° C. The polymerization pressure is generally comprised between 0.5 and 100 bar.

The lower the polymerization temperature, the higher are the resulting molecular weights of the polymers obtained.

The polymerization yields depend on the purity of the metallocene compound of the catalyst. The metallocene compounds obtained by the process of the invention can therefore be used as such or can be subjected to purification treatments.

Further object of the present invention is a ligand of formula (III)

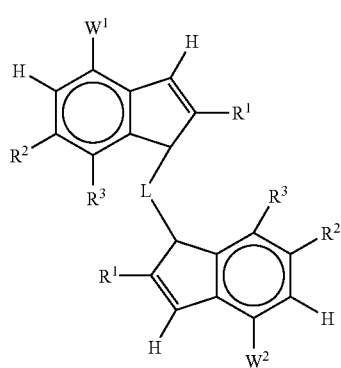

(III)

or its double bond isomers wherein L, $R^1$, $R^2$, $R^3$ $W^1$ and $W^2$ have the meaning reported above.

Preferred ligands have formulas (IIIa) or (IIIb):

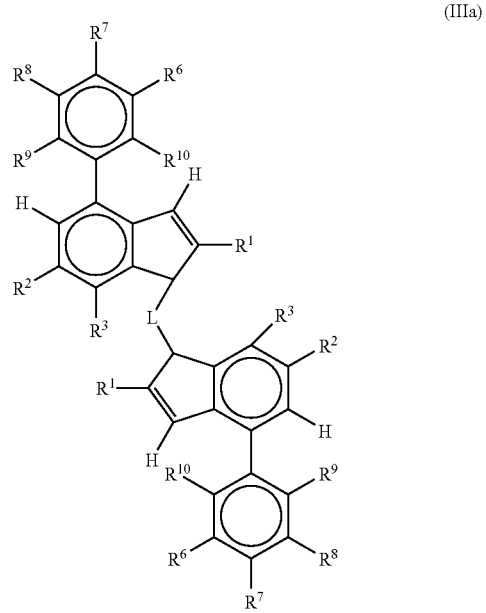

(IIIa)

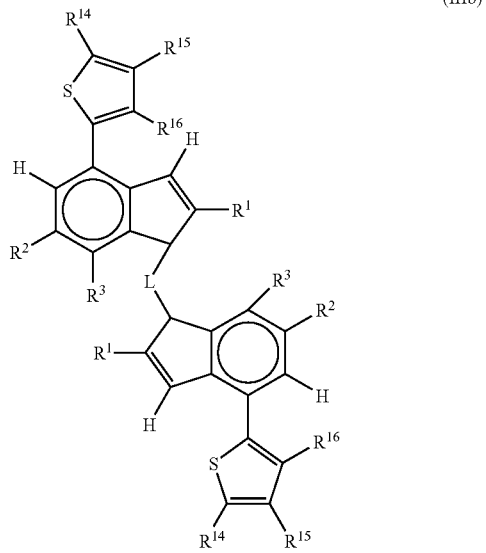

(IIIb)

or their double bond isomers wherein L, $R^1$-$R^{16}$ have the meaning reported above.

The metallocene compounds of formula (I) can be obtained with a process comprising the steps of reacting the dianion with a suitable transition metal source such as metal tetrahalide as for example zirconium tetrachloride. The dianion can be obtained for example by the deprotonation of the ligand of formula (III), for example by using an organolithium compound such as buthyl or methyl lithium. The above processes are preferably carried out in an aprotic solvent, either polar or apolar. Said aprotic solvent is preferably an aromatic or aliphatic hydrocarbon, optionally halogenated, or an ether; more preferably it is selected from benzene, toluene, pentane, hexane, heptane, cyclohexane, dichloromethane, diethylether, tetrahydrofurane and mixtures thereof. The above process is carried out at a temperature ranging from −100° C. to +80° C., more preferably from −20° C. to +70° C.

The following examples are given to illustrate and not to limit the invention.

EXAMPLES

The following examples are given to illustrate and not to limit the invention.

Examples

General characterization

Intrinsic Viscosity (I.V.) In Tetrahydronaphthalene

The intrinsic viscosity (I.V.) was measured in tetrahydronaphthalene (THN) at 135° C.

Melting Temperature ($T_m$)

Calorimetric measurements were performed by using a differential scanning calorimeter DSC Mettler. The instrument is calibrated with indium and tin standards. The weighted sample (6-8 mg), was sealed into aluminum pans, heated to 200° C. at a rate of 20° C./min and kept at that temperature for 5 minutes. Successively, after cooling at 20° C./min to 5° C. and standing for 5 minutes at 5° C., the sample was heated to 200° C. at a rate of 20° C./min. In this second heating run, the peak temperature was assumed as melting temperature ($T_m$) and the area as the global melting enthalpy ($\Delta H$).

Gel Permeation Chromatography (GPC)

Gel permeation chromatography was carried out at 135° C. in 1,2,4-trichlorobenzene using a Waters 150C GPC apparatus.

$^{13}$C-NMR Measurement

The polymer microstructure was investigated by $^{13}$C-NMR analysis. The samples were dissolved with a 8% wt/v concentration in 1,1,2,2-tetrachloroethane-$d_2$ at 120 ° C. The $^{13}$C-NMR spectra were acquired at 120° C. on a Bruker DPX400 spectrometer operating at 100.61 MHz. Each spectrum was acquired with a 90° pulse, 12 seconds of delay between pulses and CPD (WALTZ 16) to remove $^1$H-$^{13}$C coupling. About 1500 transients were stored in 32K data points using a spectral window of 6000 Hz.

In the case of isotactic polypropylene, the mmmm peak at 21.8 ppm was used as internal reference, and the pentad distribution and amounts of regioerrors were determined as described in Resconi, L.; Cavallo, L.; Fait, A.; Piemontesi, F. Chem. Rev. 2000, 100, 1253

In the case of ethylene-propylene copolymers, the assignments of the peaks were made according to Randall[1] and Tritto[2] and the triad distribution and copolymer compositions was determined according to Kakugo.[3]

The $S_{\delta\delta}$ peak at 29.9 ppm (nomenclature according to reference 4) was used as internal reference. The product of reactivity ratios $r_1 \times r_2$ was calculated from the triads according to Carman.[4]

[1] J. C. Randall, Macromol. Chem Phys. 1989, C29, 201.

[2] I. Tritto, Z. Fan, P. Locatelli, M. Sacchi, I. Camurati, M. Galimberti, Macromolecules 1995, 28, 3342.

[3] M. Kakugo, Y. Naito, K. Mizunuma, T. Miyatake, Macromolecules 1982, 15, 1150.

[4] C. J. Carman, R. A. Harrington, C. E. Wilkes, Macromolecules 1977, 10, 535.

Chemicals And Characterization

All chemicals were handled using standard Schlenk techniques.

Methylalumoxane (MAO) was received from Albemarle as a 30% wt/wt toluene solution and used as such.

Racemic-dimethylsilylbis(2-methyl-4-phenyl-inden-1-yl) dichlorozirconium (C1) was prepared according to EP 576970;

Racemic-dimethylsilylbis(2-methyl-4-(4-tert-butylphenyl)-inden-1-yl)dichlorozirconium (C2) was prepared according to WO 98/40331 (example 65).

Synthesis of rac-dimethylsilyl(2-methyl-4(4-tert-butylphenyl)-6-tert-butylinden-1-yl)dichlorozirconium (A1)

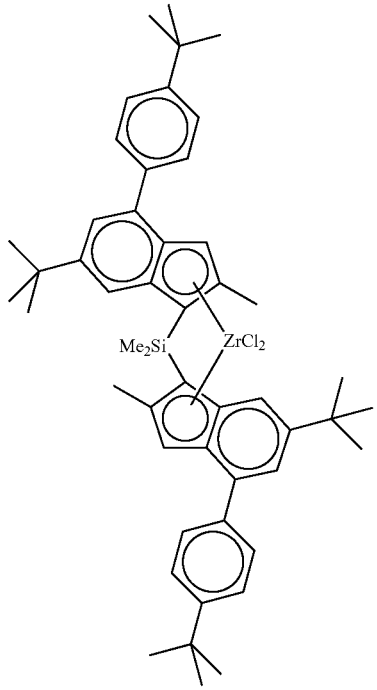

3-(2-Bromo-4-tert-butylphenyl)-2-methylpropanoic acid

N-Bromosuccinimide (98 g, 0.55 mol) and 0.5 g benzoyl peroxide were added to solution of 2-bromo-4-tert-butyl-1-methylbenzene (113.5 g, 0.5 mol) in $CCl_4$ (500 ml). The resulting mixture was refluxed for 6 h, cooled to 20° C. and filtered. The resulting filtrate was evaporated and used without further purification. A solution of sodium diethylmethylmalonate, prepared from 104.5 g (0.6 mol) diethylmethylmalonate and 40.8 g of sodium ethylate in 500 ml abs. ethanol was treated dropwise with 2-bromo-1-(bromomethyl)-4-tert-butylbenzene (0.5 mol). The resulting mixture was refluxed for 4 h, treated with a solution of NaOH (50 g, 1.25 mol) in water (60 ml) and refluxed for 2 h, then poured into water (11), and finally washed with toluene (2×100 ml). The aqueous solution was treated with 130 ml of 35% HCl. The result-

4-Bromo-6-tert-butyl-2-methyl-1-indanone

A mixture of 3-(2-bromo-4-tert-butylphenyl)-2-methyl-propanoic acid (46 g, 150 mmol) and $SOCl_2$ (18 ml, 220 mmol) was stirred for 1 h at 40° C. The excess of $SOCl_2$ was removed in vacuo. The residue was dissolved in $CH_2Cl_2$ (50 ml) and added at 0° C. to a suspension of 20 g $AlCl_3$ in $CH_2Cl_2$ (200 ml). The reaction mixture was stirred overnight, poured into ice/water (500 g) containing 50 ml of conc. HCl. The organic phase was collected, washed with water, dried over $MgSO_4$ and evaporated. The residue was distilled at 125-130° C. /0.5 torr giving 32 g (76%) of product.

$^1$H NMR ($CDCl_3$, 20° C.) δ: 7.83 (d, 1H); 7.75 (d, 1H); 3.32 (q, 1H); 2.77 (m, 1H); 2.64 (dd, 1H); 1.36 (s, 9H); 1.35 (d, 3H).

$^{13}$C NMR ($CDCl_3$, 20° C.) δ: 208.78; 153.29; 150.33; 138.00; 135.06; 121.68; 119.37; 42.26; 35.34; 34.89; 31.14; 16.18

6-tert-Butyl-4-(4-tert-butylphenyl)-2-methyl-1-indanone $Pd(OAc)_2$ (0.3 g, 3 mol %) and $PPh_3$ (0.7 g, 3 mol %) were added to a well stirred mixture 4-bromo-6-tert-butyl-2-methyl-1-indanone (12.65 g, 45 mmol), tert-butylphenylboronic acid (11.2 g, 63 mmol) and $Na_2CO_3$ (13.4 g, 126 mmol) in DME (170 ml) —$H_2O$ (56 ml). The resulting mixture was refluxed with stirring for 6 h, cooled, and poured into water. $CHCl_3$ (300 ml) was added, the organic layer was separated, washed with water, dried over $MgSO_4$, evaporated and purified by gradient column chromatography (hexane/chloroform from 4:1 to 1:1). The yield was 10.84 g (72%).

$^1$H NMR ($CDCl_3$, 20° C.) δ: 7.83 (d, 1H); 7.71 (d, 1H); 7.55 (d, 2H); 7.46 (d, 2H); 3.43 (q, 1H); 2.79 (m, 2H); 1.43 (s, 9H); 1.42 (s, 9H); 1.35 (d, 3H).

$^{13}$C NMR ($CDCl_3$, 20° C.) δ: 209.75; 151.35; 150.38; 148.34; 139.44; 136.63; 132.59; 128.05; 125.37; 119.03; 42.41; 34.77; 34.48; 34.43; 31.27; 31.23; 16.15

5-tert-Butyl-2-methyl-7-tert-butylphenyl-1H-indene 5-tert-Butyl-7-(4-tert-butylphenyl)-2-methyl-1-indanone (10.37 g, 31mmol) in $Et_2O$ (150 ml) was added dropwise at 0° C. to $LiAlH_4$ (0.6 g, 16 mmol) in $Et_2O$ (100 ml). After 1 h of stirring, 5% HCl (50 ml) was added, the organic phase was separated, the water layer was extracted in $Et_2O$ (2×50 ml). The combined organic phase was washed with aq. $Na_2CO_3$, dried over $MgSO_4$ and evaporated. The residue was dissolved in benzene (500 ml), p-TSA (1 g) was added, the resulting mixture was refluxed for 10 min, cooled, washed with water, dried over $MgSO_4$, evaporated and dried in vacuo. The yield was 9.9 g (near quantitative); yellow viscous oil.

$^1$H NMR ($CDCl_3$, 20° C.) δ: 7.61 (m, 4H); 7.43 (d, 1H); 7.32 (d ,1H); 7.64 (q, 1H); 3.48 (s, 2H); 2.24 (d, 3H); 1.51 (s, 18H).

$^{13}$C NMR ($CDCl_3$, 20° C.) δ: 150.02; 149.59; 146.34; 146.19; 138.80; 137.89; 136.49; 128.00; 127.24; 125.15; 121.47; 115.84; 42.37; 34.64; 34.44; 31.61; 31.33; 16.67

Bis(6-tert-butyl-2-methyl-4-tert-butylphenyl-1H-inden-1-yl)(dimethyl)silane

A solution of 5-tert-butyl-2-methyl-7-tert-butylphenyl-1H-indene (5.0 g, 15.7 mmol) in $Et_2O$ (70 ml) was cooled to −40° C., and n-BuLi in hexane (1.6M, 9.81 ml, 15.7 mmol) was added. The resulting mixture was allowed to warm to room temperature, stirred for 3 h, cooled to −60° C. CuCN (42 mg, 0.47 mmol) and $SiMe_2Cl_2$ (0.95 ml, 7.85 mmol) in $Et_2O$ (20 ml) were added. The resulting mixture was allowed to warm to room temperature, and stirred for 16 h. $H_2O$ (20 ml) and benzene (150 ml) were added, the organic phase was separated, dried over $MgSO_4$, passed through silica gel and evaporated. The residue was dried in vacuo (pale-yellow solid) and used in the next step without further purification.

$^1$H NMR ($CDCl_3$, 20° C.) δ: 7.62-7.40 (group of m, 12H, $C_{Ar}$—H); 6.91 (bs); 6.88 (bs) {2H, —CH=}; 3.86 (s); 3.82 (s) {2H, >CH—}; 2.31 (bs); 2.25 (bs) {6H, —C—$CH_3$}; 1.49 (s); 1.47 (s); 1.46 (s); 1.45 (s) {36H, —C($CH_3$)$_3$}; −0.06 (bs); −0.10 (bs); −0.11 (bs) {6H, Si—$CH_3$}.

Synthesis of rac-dimethylsilyl(2-methyl-4(4-tert-butylphenyl)-6-tert-butylinden-1-yl)dichlorozirconium The bis(6-tert-butyl-2-methyl-4-tert-butylphenyl-1H-inden-1-yl)(dimethyl)silane (7.85 mmol) obtained above was dissolved in $Et_2O$ (80 ml), cooled to −40° C., and n-BuLi (1.6M in hexane, 10.4 ml, 16.7 mmol) was added. The reaction mixture was allowed to warm to room temperature, stirred for 3 h, and evaporated. The resulting yellow-brown solid was suspended in pentane (200 ml), cooled to −60° C., and $ZrCl_4$ (1.94 g, 8.33 mmol) was added. After 5 min $Et_2O$ (1 ml) was added. The resulting mixture was allowed to warm to room temperature, stirred for additional 16 h, and filtered.

The residue was extracted with evaporation by pentane/$CH_2Cl_2$ (2:1) giving a mixture of isomers (1.12 g, 16.7%). This mixture was recrystallized from pentane/$CH_2Cl_2$ (5:1) yielding pure rac-form (0.11 g, 3.3%).

$^1$H NMR ($CDCl_3$, 20° C.) δ: 7.57 (bs, 2H); 7.56 ("d", 4H); 7.47 ("d", 4H); 7.46 (bs, 2H) {$C_{Ar}$—H}; 6.87 (s, 2H, H of $C_5$ ring); 2.25 (s, 6H, C—$CH_3$); 1.35 (s, 6H, Si—$CH_3$); 1.33 (s, 18H, —C($CH_3$)$_3$); 1.32 (s, 18H, —C($CH_3$)$_3$);

Preparation of the Catalyst Systems

Catalyst System S1A1

9.9 mL of TIBA/cyclohexane solution (113 g/L) were mixed with 2.4 mL of MAO/toluene solution to obtain a MAO/TIBA molar ratio of 2:1. The solution was stirred for 1 h at room temperature and transferred into a 50 mL Schlenk flask containing 20.8 mg of A1. This solution was diluted with 23.5 mL of cyclohexane to reach a concentration of 50 $g_{TOT}$/L and 0.582 $g_{metallocene}$/L.

Catalyst System S2C1

39.1 mL of TIBA/isododecane solution (90 g/L) were mixed with 7.4 mL of MAO/toluene solution to obtain a MAO/TIBA molar ratio of 2:1. The solution was stirred for 1 h at room temperature and transferred into a 50 mL Schlenk flask containing 55.8 mg of C1. The resulting mixture was diluted with 9.8 mL of isododecane to give a cloudy orange solution of concentration 100 $g_{TOT}$/L and 0.99 $g_{metallocene}$/L.

Catalyst System S3C1

39.1 mL of TIBA/cyclohexane solution (113 g/L) were mixed with 2.8 mL of MAO/toluene solution to obtain a MAO/TIBA molar ratio of 2:1. The solution was stirred for 1 h at room temperature and transferred into a 50 mL Schlenk flask containing 21.1 mg of C1. This solution was diluted with 6.78 mL of cyclohexane to give an orange solution of concentration 100 $g_{TOT}$/L and 0.99 $g_{metallocene}$/L.

Catalyst System S4C2

8.1 mL of TIBA/isododecane solution (110 g/L) were mixed with 1.9 mL of MAO/toluene solution to obtain a MAO/TIBA molar ratio of 2:1. The solution was stirred for 30 minutes at room temperature. Then, 25 mg of C2 were added to give a clear solution, which was diluted with 4.4 mL of toluene to reach a concentration of 100 $g_{TOT}$/L and 1.74 $g_{metallocene}$/L.

Propylene Polymerization Examples

The polymerization procedure and conditions for each test are described below in detail, and also collected in Table 1.

under reduced pressure at 70° C. The polymerization data are reported in table I and the characterization of the polymer obtained is reported in table 2.

Comparative Example 2

The procedure of example 1 was repeated, with the difference that 5 mL of the catalyst system S2C1 containing the catalyst/cocatalyst mixture (0.99 mg metallocene/mL solution) was injected in the autoclave by means of 4 mL of cyclohexane through the stainless-steel vial. Propylene was continuously fed for 30 minutes to maintain a pressure of 31.5 bar-g for a total consumption of 43.7 grams of propylene.

The polymer was discharged according to the procedure described in example 1. The polymerization data are reported in table 1 and the characterization of the polymer obtained is reported in table 2.

TABLE 1

| Ex | Catalyst System | metallocene (mg) | P (bar-g) | T (min) | Absorbed Propylene (g) | Activity $kg_{POL}/g_{cat}$ |
|---|---|---|---|---|---|---|
| 1 | S1A1 | 2.33 | 32 | 30 | 53 | 24.3 |
| 2* | S2C1 | 4.95 | 31.5 | 40 | 43.7 | 6.8 |

Activity in kg of polymer per gram of metallocene averaged over 30 minutes.
*Comparative example

TABLE 2

| | Analytical data on the i-PP samples. | | | | | | | | |
|---|---|---|---|---|---|---|---|---|---|
| Example | I.V. (dL/g) | $T_m$ (° C.) | mmmm (%) | mrrm (%) | 2,1 (%) | 3,1 (%) | $M_n$ $(10^{-3})$ | $M_w$ $(10^{-3})$ | $M_w/M_n$ |
| 1 | 2.1 | 150.1 | 96.1 | 0.14 | 0.5 | 0.17 | n.a. | n.a. | n.a. |
| 2* | 1.5 | 154.6 | 96.6 | 0.30 | 0.3 | 0.11 | 109 | 246 | 2.3 | n.a. not available

The results from the analysis performed on the polymer samples are collected in Table 2.

Example 1

A 4.4 L jacketed stainless-steel autoclave, equipped with a mechanically driven stirrer and a 35-mL stainless-steel vial and connected to a thermostat for temperature control, was previously purified by washing with an Al(i-Bu)$_3$ solution in hexane and dried at 50° C. in a stream of nitrogen.

6 mmol of Al(i-Bu)$_3$ (as a 100 g/L solution in hexane), 629 g of cyclohexane and 732 g of propylene were charged at room temperature, and the autoclave was then thermostated at 100° C. (the polymerization temperature). Under these conditions, the liquid composition, at 100° C., is calculated as being 50/50% wt propylene/cyclohexane.

4 mL of the catalyst system S1A1 was injected in the autoclave by means of 4 mL of cyclohexane through the stainless-steel vial. Propylene was continuously fed for 30 minutes to maintain a pressure of 32 bar-g: 53 g of propylene were consumed.

Then the bottom discharge valve of the autoclave was opened and the polymer was discharged into a heated steel tank containing water at 70° C. The tank heating was switched off and a flow of nitrogen at 0.5 bar-g was fed. After cooling at room temperature, the steel tank was opened and the wet polymer collected. The wet polymer was dried in an oven Propylene/Ethylene Copolymerization Examples Example 3

The procedure of example 1 was repeated feeding 720 g of cyclohexane, 35 g of ethylene and 654 g of propylene. 4 mL of solution of catalyst system S1A1 was injected into the autoclave by means of 4 mL of cyclohexane through the stainless-steel vial.

A mixture of ethylene/propylene 10/90% wt was continuously fed for 30 minutes to maintain the pressure of 35 bar-g: 103.4 g of propylene and 11.6 g of ethylene were consumed.

The copolymer was discharged according to the procedure described in example 1. The polymerization data are reported in table 3

Example 4

The procedure of example 1 was repeated feeding 716 g of cyclohexane, 61 g of ethylene and 631 g of propylene. 3 mL of solution of catalyst system S1A1 was injected into the autoclave by means of 4 mL of cyclohexane through the stainless-steel vial.

A mixture of ethylene/propylene 17/83% wt was continuously fed for 30 minutes to maintain the pressure of 37 bar-g: 85.1 g of propylene and 17.9 g of ethylene were consumed.

The copolymer was discharged according to the procedure described in example 1. The polymerization data are reported in table 3.

Example 5

The procedure of example 1 was repeated feeding 676 g of cyclohexane, 72 g of ethylene and 647 g of propylene. 2.5 mL of solution of catalyst system S1A1 was injected into the autoclave by means of 4 mL of cyclohexane through the stainless-steel vial.

A mixture of ethylene/propylene 21/79% wt was continuously fed for 30 minutes to maintain the pressure of 39 bar-g: 30.5 g of propylene and 8 g of ethylene were consumed. The copolymer was discharged according to the procedure described in example 1. The polymerization data are reported in table 3

Comparative Example 6

The procedure of example 1 was repeated feeding 720 g of cyclohexane, 35 g of ethylene and 654 g of propylene. 3 mL of solution of catalyst system S3C1 was injected into the autoclave by means of 4 mL of cyclohexane through the stainless-steel vial.

A mixture of ethylene/propylene 10/90% wt was continuously fed for 30 minutes to maintain the pressure of 34 bar-g: 40 g of propylene and 4.4 g of ethylene were consumed.

The copolymer was discharged according to the procedure described in example 1. The polymerization data are reported in table 3.

Comparative Example 7

The procedure of example 1 was repeated feeding 716 g of cyclohexane, 61 g of ethylene and 631 g of propylene. 4 mL of solution of catalyst system S3C1 was injected into the autoclave by means of 4 mL of cyclohexane through the stainless-steel vial.

A mixture of ethylene/propylene 17/83% wt was continuously fed for 20 minutes to maintain the pressure of 37 bar-g: 103.7 g of propylene and 21.2 g of ethylene were consumed.

The copolymer was discharged according to the procedure described in example 1. The polymerization data are reported in table 3

Comparative Example 8

The procedure of example 1 was repeated feeding 676 g of cyclohexane, 72 g of ethylene and 647 g of propylene.

2.5 mL of solution of catalyst system S3C1 was injected into the autoclave by means of 4 mL of cyclohexane through the stainless-steel vial.

A mixture of ethylene/propylene 21/79% wt was continuously fed for 30 minutes to maintain the pressure of 38 bar-g: 78.4 g of propylene and 21 g of ethylene were consumed. The copolymer was discharged according to the procedure described in example 1. The polymerization data are reported in table 3

Comparative Example 9

The procedure of example 1 was repeated feeding 958 g of cyclohexane, 31 g of ethylene and 500 g of propylene in order to obtain a liquid composition at 90° C., 21 bar-g, corresponding to a liquid composition of 5/95% wt ethylene/propylene.

4 mL of solution of the catalyst system S4C2 was injected in the autoclave by means of 4 mL of cyclohexane through the stainless-steel vial.

A mixture of ethylene/propylene 11/89% wt was continuously fed for 30 minutes to maintain the pressure of 21 bar-g: 33.7 g of propylene and 4.1 g of ethylene were consumed.

The copolymer was discharged according to the procedure described in example 1. The polymerization data are reported in table 3

Comparative Example 10

The procedure of example 1 was repeated feeding 958 g of cyclo-hexane, 50 g of ethylene and 484 g of propylene in order to obtain a liquid composition at 90° C., 24 bar-g, corresponding to a liquid composition of 8/92% wt ethylene/propylene.

4 mL of solution of the catalyst system S4C2 was injected in the autoclave by means of 4 mL of cyclohexane through the stainless-steel vial.

A mixture of ethylene/propylene 16/84% wt was continuously fed for 30 minutes to maintain the pressure of 24 bar-g: 31.2 g of propylene and 5.9 g of ethylene were consumed.

The copolymer was discharged according to the procedure described in example 1. The polymerization data are reported in table 3

Comparative Example 11

The procedure of example 1 was repeated feeding 958 g of cyclo-hexane, 64 g of ethylene and 473 g of propylene in order to obtain a liquid composition at 90° C., 26 bar-g, corresponding to a liquid composition of 10/90% wt ethylene/propylene.

4 mL of solution of the catalyst system S4C2 was injected in the autoclave by means of 4 mL of c-hexane through the stainless-steel vial.

A mixture of ethylene/propylene 20/80% wt was continuously fed for 30 minutes to maintain the pressure of 26 bar-g: 86.5 g of propylene and 21.6 g of ethylene were consumed.

The copolymer was discharged according to the procedure described in example 1. The polymerization data are reported in table 3

TABLE 3

| Ex | Cat. System | mg of zirconium compound | P (bar-g) | Activity $kg_{POL}/g_{cat}$ | ethylene content (% wt) | I.V. (dL/g) |
|---|---|---|---|---|---|---|
| 3 | S1A1 | 2.3 | 34-35 | 95.1 | 7.9 | 1.82 |
| 4 | S1A1 | 1.8 | 37 | 99.4 | 13.9 | 1.68 |
| 5 | S1A1 | 1.5 | 39 | 48.2 | 15.8 | 1.76 |
| 6* | S3C1 | 3.0 | 34 | 30.0 | 8.7 | 1.13 |
| 7* | S3C1 | 4.0 | 37 | 68.0 | 14.0 | 1.09 |
| 8* | S3C1 | 2.5 | 38 | 58.5 | 16.2 | 1.10 |
| 9* | S4C2 | 7.0 | 21 | 12.9 | 8.1 | 1.29 |
| 10* | S4C2 | 7.0 | 24 | 18.0 | 13.8 | 1.16 |
| 11* | S4C2 | 7.0 | 25.6 | 37.1 | 17.2 | 1.26 |

Activity in kg of polymer per gram of metallocene averaged over 30 minutes.
*Comparative

The invention claimed is:

1. A bridged metallocene compound of formula (I):

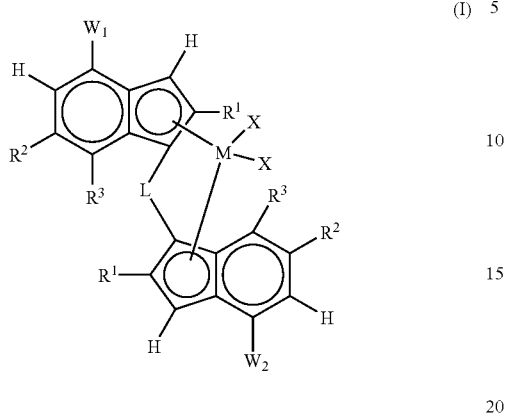

wherein:

M is an atom of a transition metal selected from those belonging to group 3, 4, or to the lanthanide or actinide groups in the Periodic Table of the Elements;

X, equal to or different from each other, is a hydrogen atom, a halogen atom, a R, OR, $OSO_2CF_3$, OCOR, SR, $NR_2$ or $PR_2$ group wherein R is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical, optionally containing heteroatoms belonging to groups 13-17 of the Periodic Table of the Elements, or two X groups can be joined together to form a group OR'O wherein R' is a $C_1$-$C_{20}$-alkylidene, $C_6$-$C_{20}$-arylidene, $C_7$-$C_{20}$-alkylarylidene, or $C_7$-$C_{20}$-arylalkylidene radical;

L is a divalent bridging group selected from $C_1$-$C_{20}$ alkylidene, $C_3$-$C_{20}$ cycloalkylidene, $C_6$-$C_{20}$ arylidene, $C_7$-$C_{20}$ alkylarylidene, or a $C_7$-$C_{20}$ arylalkylidene radicals, optionally containing heteroatoms belonging to groups 13-17 of the Periodic Table of the Elements, or it is a silylidene radical containing up to 5 silicon atoms;

$R^1$, equal to each other, are $C_1$-$C_{40}$ hydrocarbon radical optionally containing heteroatoms belonging to groups 13-17 of the Periodic Table of the Elements;

$R^2$, equal to or different from each other, are group $C(R^{19})_2R^{18}$ wherein $R^{19}$ and $R^{18}$ are linear or branched, C1-C20-alkyl radicals;

$R^3$, equal to or different from each other, are hydrogen atoms or $C_1$-$C_{40}$ hydrocarbon radicals belonging to groups 13-17 of the periodic table of the elements; and $W^1$ and $W^2$, equal or different from each other, are aromatic 5 or 6 membered rings that can contain heteroatoms belonging to groups 15-16 of the Periodic Table of the Elements, the valence of each atom of said ring is substituted with hydrogen atom or it can optionally be substituted with $R^5$ groups, wherein $R^5$, equal to or different from each other, are $C_1$-$C_{40}$ hydrocarbon radicals optionally containing heteroatoms belonging to groups 13-17 of the Periodic Table of the Elements.

2. The bridged metallocene compound according to claim 1 wherein M is zirconium, titanium or hafnium; X is a hydrogen atom, a halogen atom, a OR'O or R group; and L is $Si(R^{11})_2$ wherein $R^{11}$ is a linear or branched, cyclic or acyclic, $C_1$-$C_{10}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical.

3. The bridged metallocene compound according to claim 1 wherein W1 and W2 are selected from the group comprising the following moieties of formula (Wa), (Wb) and (Wc):

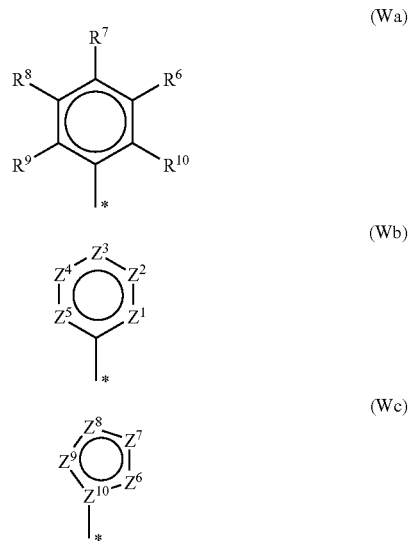

wherein the * represents the point in which the moiety bounds the indenyl moiety of the compound of formula (I);

$R^6$, $R^7$, $R^8$, $R^9$ and $R^{10}$, equal to or different from each other, are hydrogen atoms or $C_1$-$C_{40}$ hydrocarbon radicals optionally containing heteroatoms belonging to groups 13-17 of the Periodic Table of the Elements;

$Z^1$ is a nitrogen atom or a $CR^{10}$ group; $Z^2$ is a nitrogen atom or a $CR^6$ group; $Z^3$ is a nitrogen atom or a $CR^7$ group; $Z^4$ is a nitrogen atom or a $CR^8$ group; and $Z^5$ is a nitrogen atom or a $CR^9$ group, provided that no more than 2 groups among $Z^1$, $Z^2$, $Z^3$, $Z^4$ and $Z^5$ are nitrogen atoms;

$Z^6$ is an oxygen atom, a sulfur atom, a $NR^{13}$ group or a $CR^{13}$ group; $Z^7$ is an oxygen atom, a sulfur atom, a $NR^{14}$ group or a $CR^{14}$ group; $Z^8$ is an oxygen atom, a sulfur atom, a $NR^{15}$ group or a $CR^{15}$ group; $Z^9$ is an oxygen atom, a sulfur atom, a $NR^{16}$ group or a $CR^{16}$ group;

$Z^{10}$ is a nitrogen atom or a carbon atom that bonds the indenyl moiety of the structure of formula (I); with the proviso that not more than 1 group among $Z^6$, $Z^7$, $Z^8$, $Z^9$ or $Z^{10}$ is a sulfur atom, an oxygen atom or a nitrogen-containing group atom selected from $NR^{13}$, $NR^{14}$, $NR^{15}$, $NR^{16}$, and a nitrogen atom;

$R^{13}$, $R^{14}$, $R^{15}$ and $R^{16}$, equal to or different from each other, are hydrogen atoms or $C_1$-$C_{40}$ hydrocarbon radicals optionally containing heteroatoms belonging to groups 13-17 of the Periodic Table of the Elements.

4. The bridged metallocene compound according to claim 3 wherein in the moiety of formula (Wa), $R^7$ is a $C_1$-$C_{40}$-alkyl radical, and $R^6$, $R^8$, $R^9$ and $R^{10}$ are hydrogen atoms.

5. The bridged metallocene compound according to claim 3 wherein in the moiety of formula (Wa), $R^{10}$ and $R^8$ are $C_1$-$C_{40}$-alkyl radicals, and $R^7$, $R^8$ and $R^9$ are hydrogen radicals.

6. The bridged metallocene compound according to claim 3 wherein in the moiety of formula (Wa), $R^6$, $R^7$ and $R^8$ are linear or branched $C_1$-$C_{40}$-alkyl radicals and $R^{10}$ and $R^9$ are hydrogen atoms.

7. The bridged metallocene compound according to claim 3 wherein in the moiety of formula (Wa), $R^6$, $R^7$, $R^8$, $R^9$ and $R^{10}$ are hydrogen atoms.

8. The bridged metallocene compound according to claim 3 wherein in the moiety of formula (Wb), $Z^1$ is a nitrogen atom and $Z^2$, $Z^3$, $Z^4$ and $Z^5$ are respectively $CR^6$, $CR^7$, $CR^8$ and $CR^9$.

9. The bridged metallocene compound according to claim 3 wherein in the moiety of formula (Wb), $Z^3$ is a nitrogen atom and $Z^1$, $Z^2$, $Z^4$ and $Z^5$ are respectively $CR^{10}$, $CR^6$, $CR^8$ and $CR^9$.

10. The bridged metallocene compound according to claim 3 wherein in the moiety of formula (Wb), $Z^2$ is a nitrogen atom and $Z^1$, $Z^3$, $Z^4$ and $Z^5$ are respectively $CR^{10}$, $CR^7$, $CR^8$ and $CR^9$.

11. The bridged metallocene compound according to claim 3 wherein in the moiety of formula (Wc), $Z^6$ is an oxygen atom, a sulfur atom, or a $NR^{16}$ group.

12. The bridged metallocene compound according to claim 1 having formula (IIa):

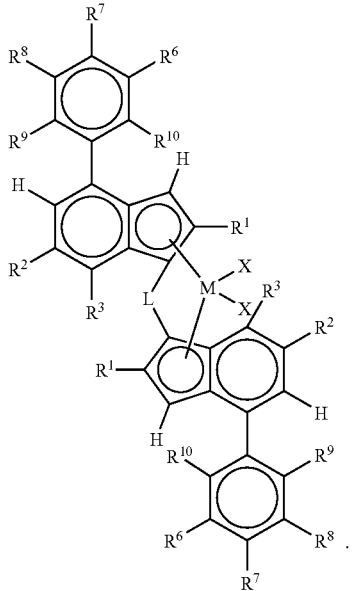

(IIa)

13. The bridged metallocene compound according to claim 1 having formula (IIb):

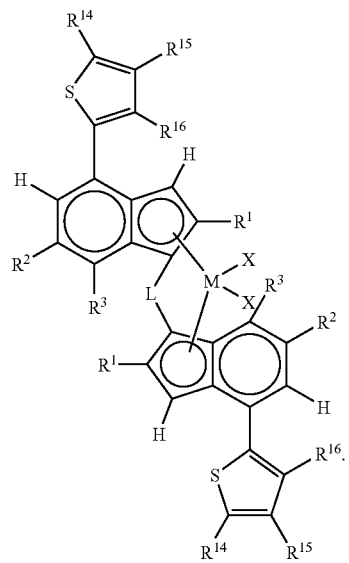

(IIb)

14. A process for preparing an alpha-olefin polymer comprising contacting under polymerization conditions at least one alpha-olefin of formula $CH_2=CHA$ wherein A is hydrogen or a $C_1$-$C_{20}$ alkyl radical, in the presence of a catalyst system having formula (IIb):

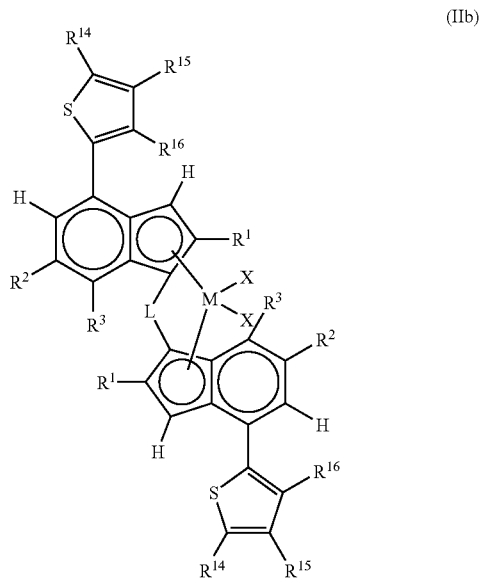

(IIb)

wherein:
M is an atom of a transition metal selected from those belonging to group 3, 4, or to the lanthanide or actinide groups in the Periodic Table of the Elements;

X, equal to or different from each other, is a hydrogen atom, a halogen atom, a R, OR, $OSO_2CF_3$, OCOR, SR, $NR_2$ or $PR_2$ group wherein R is a linear or branched, cyclic or acyclic, $C_1$-$C_{40}$-alkyl, $C_2$-$C_{40}$ alkenyl, $C_2$-$C_{40}$ alkynyl, $C_6$-$C_{40}$-aryl, $C_7$-$C_{40}$-alkylaryl or $C_7$-$C_{40}$-arylalkyl radical, optionally containing heteroatoms belonging to groups 13-17 of the Periodic Table of the Elements, or two X groups can be joined together to form a group OR'O wherein R' is a $C_1$-$C_{20}$-alkylidene, $C_6$-$C_{20}$-arylidene, $C_7$-$C_{20}$-alkylarylidene, or $C_7$-$C_{20}$-arylalkylidene radical;

L is a divalent bridging group selected from $C_1$-$C_{20}$ alkylidene, $C_3$-$C_{20}$ cycloalkylidene, $C_6$-$C_{20}$ arylidene, $C_7$-$C_{20}$alkylarylidene, or a $C_7$-$C_{20}$ arylalkylidene radicals, optionally containing heteroatoms belonging to groups 13-17 of the Periodic Table of the Elements, or it is a silylidene radical containing up to 5 silicon atoms;

$R^1$, equal to each other, are $C_1$-$C_{40}$ hydrocarbon radical optionally containing heteroatoms belonging to groups 13-17 or the Periodic Table of the Elements;

$R^2$, equal to or different from each other, are branched, cyclic or acyclic, alkyl, alkenyl, or alkynyl radicals containing from 3 to 40 carbon atoms, optionally containing heteroatoms belonging to groups 13-17 of the periodic table of the elements; $R^3$, equal to or different from each other, are hydrogen atoms or $C_1$-$C_{40}$ hydrocarbon radicals belonging to groups 13-17 of the periodic table of the elements;

$W^1$ and $W^2$, equal or different from each other, are aromatic 5 or 6 membered rings that can contain heteroatoms belonging to groups 15-16 of the Periodic Table of the Elements, the valence of each atom of said ring is substituted with hydrogen atom or it can optionally be substituted with $R^5$ groups, wherein $R^5$, equal to or different from each other, are $C_1$-$C_{40}$ hydrocarbon radicals optionally containing heteroatoms belonging to groups 13-17 of the Periodic Table of the Elements.

15. The process according to claim 14 wherein propylene is (co)polymerized.

16. The process according to claim 14 wherein propylene is copolymerized with ethylene.

* * * * *